US008263077B2

(12) United States Patent
Aburatani et al.

(10) Patent No.: US 8,263,077 B2
(45) Date of Patent: Sep. 11, 2012

(54) CELL GROWTH INHIBITORS CONTAINING ANTI-GLYPICAN 3 ANTIBODY

(75) Inventors: Hiroyuki Aburatani, Musashino (JP);
Tetsuo Nakamura, Bunkyo-ku (JP);
Masayuki Tsuchiya, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/799,491

(22) Filed: Apr. 26, 2010

(65) Prior Publication Data

US 2011/0002922 A1  Jan. 6, 2011

Related U.S. Application Data

(63) Continuation of application No. 11/702,780, filed on Feb. 5, 2007, now Pat. No. 7,744,880, which is a continuation of application No. 10/481,524, filed as application No. PCT/JP02/06237 on Jun. 21, 2002, now abandoned.

(30) Foreign Application Priority Data

Jun. 22, 2001 (JP) ................................ 2001-189443

(51) Int. Cl.
*A61K 31/00* (2006.01)
*A61K 38/00* (2006.01)
*A61K 38/16* (2006.01)
*A61K 39/00* (2006.01)
*A61K 39/395* (2006.01)
*A61K 49/00* (2006.01)
*A01N 37/118* (2006.01)
*A01N 61/00* (2006.01)

(52) U.S. Cl. .... 424/138.1; 424/9.1; 424/9.2; 424/130.1; 424/133.1; 514/1; 514/2; 514/8

(58) Field of Classification Search .................. None
See application file for complete search history.

(56) References Cited

U.S. PATENT DOCUMENTS

| 6,214,973 | B1 | 4/2001 | Ohtomo et al. ............ 530/387.1 |
| 6,327,353 | B1 | 12/2001 | Fukuzawa et al. |
| 7,361,336 | B1 | 4/2008 | Bergstein |
| 7,427,400 | B2 | 9/2008 | Bergstein |
| 7,744,880 | B2 * | 6/2010 | Aburatani et al. ......... 424/138.1 |
| 2003/0045691 | A1 | 3/2003 | Ono et al. ................ 530/388.85 |
| 2003/0103970 | A1 | 6/2003 | Tsuchiya |
| 2006/0008456 | A1 | 1/2006 | Tsuchiya et al. ........... 424/133.1 |
| 2006/0193828 | A1 | 8/2006 | Kosaka et al. ............... 424/85.6 |

FOREIGN PATENT DOCUMENTS

| JP | 4228089 | 10/1992 |
| JP | 10155494 | 6/1998 |
| JP | 11-355440 | 12/1999 |
| JP | 2007238632 | 9/2007 |
| WO | 9633735 | 10/1996 |
| WO | WO 99/18212 | 4/1999 |
| WO | WO 01/13940 | 3/2001 |

OTHER PUBLICATIONS

Chung, Maxey C. M. et al., "P roteomics of Hepatocellular Carcinoma: Present Status and Future Prospects," *Proteomics: Biomedical and Pharmaceutical Applications*, (2004), pp. 163-181.
Igaku, Saishin, *The Medical Frontline* 59(6), (2004), pp. 135-143 (with English Translation).
Kurokawa, Yukinori et al., "Molecular features of a non-B, non-C hepatocellular carcinoma; a PCR-array gene expression profiling study," *Journal of Hepatology*, 39 (2003), pp. 1004-1012.
Kensa, Rinsho et al., *Clinical Laboratory Investigation*, vol. 44, No. 13 (2000), pp. 1649-1657 (with English Translation).
Takels-Horne, Darci et al., "Iden tification of Differentially Expressed Genes in Hepatocellular Carcinoma and Metastatic Liver Tumors by Oligonucleotide Expression Profiling," *Cancer*, vol. 92, No. 2 (2001), pp. 395-405.
Tannapfel, Andrea et al., "Genes involved in hepatocellular carcinoma; deregulation in cell cycling and apoptosis," *Virchows Arch*, No. 440 (2002), pp. 345-352.
Honda, Masao et al., *Molecular Medicine*, vol. 39, No. 8 (2002), pp. 938-946 (with English Translation).
Kawai, Hiroshi et al., *Pharma Medica*, vol. 20, No. 2 (2002), pp. 51-59 (with English Translation).
Honda, Masao et al. *Liver Gallbladder and Pancreas*, vol. 48, No. 4 (2004), pp. 447-453 (with English Translation).
Goldenberg, Daniel et al., "An alysis of Differentially Expressed Genes in Hepatocellular Carcinoma Using cDNA Arrays," *Molecular Carcinogenesis*, vol. 33 (2002), pp. 113-124).
Lage, Hermann et al., "Exp ression of glypican-related 62kDa antigen is decreased in hepatocellular carcinoma in correspondence to the grade of tumor differentiation," *Virchows Arch*, vol. 438 (2001), pp. 567-573.
Office Action issued on Jan. 22, 2008 in connection with U.S. Appl. No. 11/414,676.
Timer, Jozsef et al., "Proteoglycans and tumor progression: Janus-faced molecules with contradictory functions in cancer," *Seminars in Cancer Biology*, vol. 12 (2002), pp. 173-186.
Powell, Charles A., et al., "Oligonucleotide Microarray Analysis of Lung Adenocarcinoma in Smokers and Nonsmokers Identifies GPC3 as a Potential Lung Tumor Suppressor," *Chest*, vol. 121, Suppl. 3, (2002) pp. 6S-7S.
Kim, Han et al., "T he Heparan Sulfate Proteoglycan *GPC3* is a Potential Lung Tumor Suppressor," *American Journal of Respiratory Cell and Molecular Biology*, vol. 29, No. 6 (2003), pp. 694-701.
White, GRM et al., "Somatic Glypican 3 (GPC3) mutations in Wilms' tumour," *British Journal of Cancer*, vol. 86, No. 12 (2002), pp. 1920-1922.
Veugelers, Mark et al., "The Glypicans: a Family of GPI-Anchored Heparan Sulfate Proteoglycans with a Potential Role in the Control of Cell Division," *Trends in Glycoscience and Glycotechnology*, vol. 10, No. 52 (1998), pp. 145-152.
Office Action dated Nov. 11, 2008 issued in corresponding Japanese Patent Application No. 2008-228128.

(Continued)

*Primary Examiner* — Alana Harris Dent
(74) *Attorney, Agent, or Firm* — Davidson, Davidson & Kappel, LLC

(57) ABSTRACT

Provided is a cell growth inhibitor that can be used for treating diseases based on abnormal cell proliferation, and in particular cancer. The cell growth inhibitor contains an anti-glypican 3 antibody as an active ingredient.

5 Claims, 10 Drawing Sheets

OTHER PUBLICATIONS

"AAC R American Association for Cancer Research", 93rd Annual Meeting, Apr. 6-10, 2002—San Francisco, California, vol. 43—Mar. 2002.

Pilia, et al., Mutations in GPC3, a glypican gene, cause the Simpson-Golabi-Behmel overgrowth syndrome, Giuseppe Pilia, Nature Genetics, vol. 12, Mar. 1996.

Gonzalez, et al., OCI-5/GPC3, a Glypican Encoded by a Gene That Is Mutated in the Simpson-Golabi-Behmel Overgrowth Syndrome, Induces Apoptosis in a Cell Line-specific Manner, Journal of Cell Biology, vol. 141, No. 6, Jun. 15, 1998 1407-1414.

Lage, et al., Cloning and characterization of human cDNAs encoding a protein with high homology to rat intestinal development protein OCI-5, Gene, vol. 188, pp. 151-156, 1997.

Zhu, et al., Enhanced glypican-3 expression differentiates the majority of hepatocellular carcinomas from benign hepatic disorders, Oct. 17, 2000, GUT vol. 48, pp. 558-564.

Chin J. Surg, Mar. 1999, vol. 37, No. 3.

Saikali, et al., Expression of Glypican 3 (GPC3) in Embryonal Tumors, Int. J. Cancer, vol. 89, pp. 418-422 (2000).

Filmus, Glypicans in growth control and cancer, Glycobiology vol. 11 No. 3 pp. 19R-23R, 2001.

Lin, et al., Frequent Silencing of the GPC3 Gene in Ovarian Cancer Cell, Cancer Research 59, 807-810 Feb. 15, 1999.

Hsu et al., Cloning and Expression of a Developmentally Regulated Transcript MXR7 in hepatocellular carcinoma, vol. 57, pp. 5179-5189 (1997).

Mariana Isabel Capurro, et al., Overexpression of Glypican-3 in Human hepatocellular carcinomas determined by immunohistochemistry using a monoclonal antibody, Proceedings of the American Association for Cancer Research, vol. 43, Mar. 2002.

Xu Y, et al. , Developmental Regulation of the Soluble Form of Insulin-like Growth Factor-II/mannose 6-Phosphate Receptor in Human Serum and Amniotic Fluid, Journal of Clinical Endocrinology and Metabolism, Feb. 1998, vol. 83, No. 2, pp. 437-442, XP002959807.

Abstract, Kleeff J.H., et al., Glypican-3 is a Potential Tumore Marker for Hepatocellular Carcinoma, Gastroenterology, W.B. Saunders Company, Philadelphia, U.S., vol. 118, No. 4, Suppl. 2, Part 1, 2000, pp. A261, XP-002959809.

Abstract, Lage H., et al., Glypican-3 Contributes to a Mitoxantrone-Resistant Phenotype in Gastric Carcinoma Cells, Proceedings of the American Association for Cancer Research, vol. 42, Mar. 2001, p. 279, printed from Database Biosis Online! Biosciences Information Service, Philadelphia, PA, U.S., XP001203974.

Herman Lage et al., Expression of a glypican-related 62-kDa antigen is decreased in hepatocellular carcinoma in correspondence to the grade of tumor differentiation, Virchows Arch, vol. 438, pp. 567-573, Feb. 21, 2001.

Freshney, Culture of Animal Cells, A manual of Basic Technique, Alan R. Liss, Inc., 1983, New York, p. 4.

Dermer, Biotechnology, 1994, vol. 12, p. 320.

Drexler, Leukemia and Lymphoma, 1993, vol. 9, pp. 1-25.

Zellner et al., Clinical Cancer Research, 1998, vol. 4, pp. 1797-1802.

Embleton et al., Immunology Series, 1984, vol. 23, pp. 181-207.

Hsu, in Tissue Culture Methods and Applications, Kruse and Patterson, Eds, 1973, Academic Press, NY, abstract.

Gura, Science, 1997, vol. 278, pp. 1041-1042.

Jain, Scientific American, 1994, vol. 271, pp. 58-65.

Curti, Critical Review in Oncology and Hematology, 1993 vol. 14, pp. 29-39.

Sanchez-Mejorada et al., Journal Leukocyte Biology, 1998, vol. 63, pp. 521-533.

Huber, PhD Dissertation, Washington University, Dec. 1998.

Johnstone and Thorpe, Immunochemistry in Practice, Blackwell Scientific Publications, Oxford, 1987, p. 49-50.

Queen et al., Proceeding of the National Academy of Science, 1989, vol. 86, pp. 10029-10033.

Reichmann et al., Nature, 1988, vol. 332, pp. 323-327.

Carter, Paul. Improving the efficacy of antibody-based cancer therapies. Nature 1: 118-129, Nov. 2001.

Zhu et al. Enhanced glypican-3 expression differentiates the majority of hepatocellular carcinomas from benign hepatic disorders. Gut 48: 558-564, Apr. 2001.

Goldenberg DM and Sharkey RM. Novel radiolabeled antibody conjugates. Oncogene. May 28, 2007; 26(25): 3734-44.

Johnson and Goldin (Cancer Treatment Reviews 2: 1-31, 1975).

Bodey B. et al. Genetically engineered monoclonal antibodies for direct anti-neoplastic treatment and cancer cell specific delivery of chemotherapeutic agents. Curr Pharm Des. Feb. 2000; 6(3): 261-76.

De Cat, Bart et al., "Developmental roles of the glypicans", Seminars in Cell & Developmental Biology, Apr. 2001, vol. 12, pp. 117-125.

Pellegrini, Massimo et al., "Gpc3 Expression Correlates with the Phenotype of the Simpson-Golabi—Behmel Syndrome", Developmental Dynamics, 1998, vol. 213, pp. 431-439.

Eccles, Suzanne A., "Monoclonal antibodies targeting cancer: 'magic bullets' or just the trigger?", Breast Cancer Res., Dec. 2000 , vol. 3, pp. 86-90.

Cragg, Mark S. et al., "Signaling antibodies in cancer therapy", Current Opinion in Immunology, 1999, vol. 11, pp. 541-547.

Lewis, Gail D. et al., "Differential response of human tumor cell lines to anti-p185$^{HER2}$ monoclonal antibodies", Cancer Immunol. Immunother., 1993, vol. 37, pp. 255-263.

Grillo-Lopez, A.J. et al., "Rituximab: The First Monoclonal Antibody Approved for the Treatment of Lymphoma", Current Pharmaceutical Biotechnology, 2000, vol. 1 , p. 1-9.

"Fundamental study Pertaining to ADCC with monoclonal antibody to tumor-associated antigen", Medical care and New medicines, 1982, Vol.19, No. 3, pp. 473-478 (with partial English translation).

Saxena, R.K. et al., "Identity of effector cells participating in the reverse antibody-dependent cell mediated cytotoxicity", Immunology, 1982, vol.46, pp. 459-464.

Lamon, E.W., et al. "Antibody-Dependent Cell-Mediated Cytotoxicity in the Moloney Sarcoma Virus System: Differential Activity of IgG and IgM with Different Subpopulations of Lymphocytes", J. Exp. Med., 1977, vol. 145, pp. 302-313.

Carter, Paul et al., "Identification and validation of cell surface antigens for antibody targeting in oncology", Endocrine-Related Cancer, 2004, vol. 11, pp. 659-687.

Chen, Guoan et al., "Discordant Protein and mRNA Expression in Lung Adenocarcinomas", Molecular & Cellular Proteomics, 2002, vol. 1 , pp. 304-313.

Smith, Duncan L. et al., "Changes in the Proteome Associated with the Action of Bcr-Abl Tyrosine Kinase Are Not Related to Transcriptional Regulation", Molecular & Cellular Proteomics, 2002, vol. 1 , pp. 876-884.

Xu, Jiangchun et al., "Identification of Differentially Expressed Genes in Human Prostate Cancer Using Substraction and Microarray", Cancer Res., 2000, vol. 60, pp. 1677-1682.

Wang, Tongtong et al., "Identification of genes differentially overexpressed in lung squamous cell carcinoma using combination of cDNA substraction and microarray analysis", Oncogene, 2000, vol. 19, pp. 1519-1528.

Sgroi, Dennis C. et al., "In Vivo Gene Expression Profile Analysis of Human Breast Cancer Progression", Cancer Res. 1999, vol. 59, pp. 5656-5661.

Office Action dated Dec. 14, 2010 issued in corresponding Japanese Patent Application No. 2007-165739.

Office Action, dated Nov. 22, 2011, issued in connection with corresponding Japanese Patent Application No. 2009-105835, Action in Japanese.

Roitt, Ivan et al., Immunology (Fifth Edition), Nankodo, 2000, p. 72-73, 76-77, and 78-79.

Osawa, Toshiaki et al., Dictionary of Immunology (Second Edition), Tokyokagakudojin, 2001, p. 243, 560.

\* cited by examiner

U-937

Ramos

MLMA

CELL GROWTH INHIBITORS CONTAINING ANTI-GLYPICAN 3 ANTIBODY

This application is a continuation of U.S. patent application Ser. No. 11/702,780 filed Feb. 5, 2007, which issued on Jun. 29, 2010 as U.S. Pat. No. 7,744,880, which is a continuation of U.S. patent application Ser. No. 10/481,524 filed Jun. 30, 2004, which is a national phase application of PCT/JP02/06237, filed Jun. 21, 2002, the disclosures of which are hereby incorporated by reference in their entireties.

FIELD OF THE INVENTION

The present invention relates to a cell growth inhibitor containing an anti-glypican 3 antibody as an active ingredient.

BACKGROUND OF THE INVENTION

The glypican family has been reported to be present as a new family of heparan sulfate proteoglycans that are present on cell surfaces. To date, the 5 types of glypicans (glypican 1, glypican 2, glypican 3, glypican 4 and glypican 5) have been reported as members of the glypican family. These members of the family have core proteins of uniform size (approximately 60 kDa), share specific and well-conserved cysteine sequences, and bind to cell membranes via glycosyl phosphatidyl inositol (GPI) anchors.

A Dally (division abnormally delayed) gene has been identified by screening for genes of a variant of *Drosophila melanogaster* having an abnormal cell division pattern in the development of the central nervous system. The cDNA of Dally is known to represent an open reading frame (ORF) encoding a product having a sequence that shows homology (24 to 26% homology) with a membrane-spanning proteoglycan (GRIPs) of a vertebrate containing all the features of a glypican. It has been then suggested that the dally gene plays a role in regulating the dpp (decapentaplegia) receptor mechanism. This suggests that the glypican of a mammal may regulate the signal transduction between TGF and BMP. Specifically, it has been suggested that glypican may function as a common receptor for some of heparin-binding growth factors (e.g., EGF, PDGF, BMP2 and FGF's).

Glypican 3 has been isolated as a transcript under developmental regulation in rat intestine (Filmus, J., Church, J. G., and Buick, R. n. (1988) Mol. Cell Biol. 8, 4243-4249), and then identified as OCT-5, a GPI-linked heparan sulfate proteoglycan of the glypican family, which has a core protein with a molecular weight of 69 kDa (Filmus, J., Shi, W., Wong, Z.-M., and Wong, M. J. (1995) Biochem. J. 311, 561-565). Also in humans, a gene encoding glypican 3 has been isolated as MXR-7 from a human gastric cancer cell line (Hermann Lage et al., Gene 188 (1997) 151-156). Glypican 3 has been reported to form a protein-protein complex with an insulin-like growth factor-2 so as to regulate the action of the growth factor (Pilia, G. et al, (1996) Nat. Genet. 12, 241-247). This report suggests that glypican 3 does not always interact with growth factor having the heparan sulfate chain.

There has been a report suggesting that glypican 3 may be utilized as a hepatic cancer marker (Hey-Chi Hsu et al., CANCER RESEARCH 57, 5179-5184 (1997)). However, there is no finding indicating a clear relationship between glypican 3 and the proliferation of carcinoma cells.

Moreover, it has also been suggested that glypican may function as a receptor for endostatin that may act as a vascularization inhibitor (Molecular Cell (2001), 7, 811-822). However, the relationship between this function and cell proliferation has not been elucidated either.

As described above, the involvement of glypican 3 in cell proliferation has been suggested. However, the cell proliferation mechanism and the like are unknown, and the application of glypcian 3 for the regulation of cell proliferation has never been attempted.

SUMMARY OF THE INVENTION

An object of the present invention is to provide a cell growth inhibitor containing an anti-glypican 3 antibody as an active ingredient.

As a result of intensive studies, we have completed the present invention by finding that the anti-glypican 3 antibody exerts cell proliferation-inhibiting activity by ADCC (antibody-dependent cell-mediated cytotoxicity) activity and CDC (complement-dependent cytotoxicity) activity. Furthermore, it is also predicted that anti-glypican 3 antibodies also exert cell proliferation-inhibiting activity by inhibiting the action of a growth factor. Furthermore, anti-glypican 3 antibodies can also exert cell proliferation-inhibiting activity by binding with cytotoxic substances such as a radioactive isotope, a chemotherapeutant or toxin derived from bacteria.

The present invention is as follows:

(1) A cell growth inhibitor, containing an anti-grlypican 3 antibody as an active ingredient;
(2) The cell growth inhibitor of (1), wherein the anti-glypican 3 antibody has cytotoxic activity;
(3) The cell growth inhibitor of (2), wherein the cytotoxic activity is antibody-dependent cell-mediated cytotoxicity (ADCC) activity or complement-dependent cytotoxicity (CDC) activity;
(4) The cell growth inhibitor of any one of (1) to (3), wherein the cells are carcinoma cells;
(5) The cell growth inhibitor of (4), wherein the cells are selected from the group consisting of hepatic cancer cells, lung cancer cells, colon cancer cells, mammary cancer cells, prostate cancer cells, leukemia cells, lymphoma cells and pancreatic cancer cells;
(6) The cell growth inhibitor of (5), wherein the cells are hepatic cancer cells;
(7) The cell growth inhibitor of any one of (1) to (6), wherein the antibody is a monoclonal antibody;
(8) The cell growth inhibitor of any one of (1) to (6), wherein the antibody is a humanized antibody or a chimeric antibody;
(9) An antibody, binding to glypican 3;
(10) The antibody of (9), having cytotoxic activity;
(11) The antibody of (10), having cytotoxic activity against hepatic cancer cells; and
(12) The antibody of (11), having cytotoxic activity against an HuH-7 hepatic cancer cell line.

The present invention will be described in detail below.

The present invention is a cell growth inhibitor containing an anti-glypican antibody as an active ingredient. Furthermore, the present invention is a cell growth inhibitor containing the anti-glypican antibody as an active ingredient that can be used for the therapy against diseases based on abnormal cell proliferation, and particularly against cancer.

Examples of the anti-glypican 3 antibody of the present invention include a known antibody such as a humanized antibody, a human antibody (WO96/33735), a chimeric antibody (JP Patent Publication (Kokai) No. 4-228089 A (1992)) or a mouse antibody, as well as antibodies in the present invention. In addition, an antibody may be a polyclonal antibody, and is preferably a monoclonal antibody.

The anti-glypican 3 antibody used in the present invention may be derived from any origin, may be of any type (monoclonal or polyclonal) and may be in any form, as long as it is capable of inhibiting cell proliferation.

1. Anti-Glypican 3 Antibody

The anti-glypican 3 antibody used in the present invention can be obtained by a known means as a polyclonal or a monoclonal antibody. A particularly preferred anti-glypican 3 antibody used in the present invention is a monoclonal antibody derived from a mammal. Examples of the monoclonal antibody derived from a mammal include an antibody produced by a hybridoma and an antibody produced by a host transformed using an expression vector containing the antibody gene by genetic engineering techniques. This antibody binds to glypican 3 so as to inhibit cell proliferation.

An example of such an antibody is a monoclonal antibody produced by the hybridoma clone of the present invention.

2. Antibody-Producing Hybridoma

A monoclonal antibody-producing hybridoma can be basically prepared using known techniques as follows. That is, the hybridoma can be prepared by performing immunization using glypican 3 as an immunogen according to a standard immunization method, causing the thus obtained immunocytes to fuse with known parent cells by a standard cell fusion method, and then screening for monoclonal antibody-producing cells by a standard screening method.

Specifically, monoclonal antibodies can be prepared as follows.

Human glypican 3 to be used as an immunogen to obtain antibodies is first obtained by expressing the glypican 3 (MXR7) gene (amino acid sequence) as disclosed by Lage, H. et al (Gene 188 (1997), 151-156). Specifically, the gene sequence encoding glypican 3 is inserted in a known expression vector system, an appropriate host cell is transformed, and then a target human glypican 3 protein is purified by a known method from the host cells or the culture supernatant.

Next, this purified glypican 3 protein is used as an immunogen. Alternatively, the partial peptide of glypican 3 can be used as a sensitization antigen. At this time, the partial peptide can be obtained by chemical synthesis from the amino acid sequence of human glypican 3.

Anti-glypican 3 antibody inhibits cell proliferation activity with the ADCC action, the CDC action and the activity of a growth factor. Moreover, the anti-glypican 3 antibody can also inhibit cell proliferation by binding with a cytotoxic substance such as a radioisotope, a chemotherapeutant or a toxin derived from bacteria. Hence, in the present invention, an epitope on a glypican 3 molecule which is recognized by the anti-glypican 3 antibody is not limited to a particular epitope. The anti-glypican 3 antibody may recognize any epitope, as long as the epitope is present on a glypican 3 molecule. Accordingly, any fragment can be used as an antigen for preparing the anti-glypican 3 antibody of the present invention, as long as it contains the epitope on a glypican 3 molecule.

A mammal to be immunized with an immunogen is not specifically limited, and is preferably selected in consideration of compatibility with a parent cell to be used for cell fusion. For example, rodents such as mice, rats, hamsters or rabbits, or monkeys are generally used.

Animals are immunized with an immunogen according to a known method. For example, immunization is performed by a general method wherein a mammal is injected intraperitoneally or subcutaneously with an immunogen. Specifically, an immunogen is diluted with or suspended in an appropriate volume of PBS (Phosphate-Buffered Saline), physiological saline or the like; an appropriate volume of a standard adjuvant such as a Freund's complete adjuvant is mixed with the product if necessary; emulsification is performed; and then the solution is administered to mammals several times every 4 to 21 days. In addition, an appropriate carrier can also be used upon immunization with an immunogen.

Mammals are immunized as described above, and then an increased titer of a desired antibody in the serum is confirmed. Subsequently, immunocytes are collected from the mammals, and then subjected to cell fusion. A preferred immunocyte is particularly a splenocyte.

As a partner cell to be fused with the above immunocyte, a mammalian myeloma cell is used. Examples of a cell line of a myeloma cell that is preferably used herein include various known cell lines such as P3 (P3x63Ag8.653) (J. Immnol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323) and R210 (Galfre, G. et al., Nature (1979) 277, 131-133).

Cell fusion of the above immunocytes with myeloma cells can be basically performed according to a known method, for example, the method of Kohler and Milstein et al (Kohler. G. and Milstein, C., Methods Enzymol. (1981) 73, 3-46).

More specifically, the above cell fusion is performed in a standard nutrition culture solution in the presence of, for example, a cell-fusion accelerator. As a cell-fusion accelerator, for example, polyethylene glycol (PEG), hemagglutinating virus of Japan (HVJ) or the like is used. If desired, an adjuvant such as dimethylsulfoxide can also be used by addition to further enhance fusion efficiency.

Any ratio of immunocytes to myeloma cells may be set for use herein. For example, it is preferable that the number of immunocytes be 1 to 10 times greater than that of myeloma cells. As a culture solution to be used for the above cell fusion, for example, a RPMI1640 culture solution or a MEM culture solution which is appropriate for the growth of the above myeloma cell line, or other standard culture solutions that are used for this type of cell culture can be used. Moreover, a serum fluid such as fetal calf serum (FCS) can be used in combination therewith.

Cell fusion is performed by mixing sufficiently certain amounts of the above immunocytes and myeloma cells in the above culture solution, adding a PEG (e.g., with an average molecular weight of approximately 1000 to 6000) solution (a general concentration of 30 to 60% (w/v)) pre-heated at approximately 37° C. with, and then mixing the solution, so as to form target fused cells (hybridomas). Subsequently, an appropriate culture solution is added successively, and then a step of removing the supernatant by centrifugation is repeated, so that reagents for cell fusion or the like that is unfavorable for the growth of the hybridomas is removed.

The thus obtained hybridomas are selected by culturing the hybridomas in a standard selective culture solution such as a HAT culture solution (a culture solution containing hypoxanthine, aminopterin and thymidine). Culture in the above HAT culture solution is continued for a time period sufficient for the cells (unfused cells) other than the target hybridomas to die (normally, several days to several weeks). Subsequently, a standard limiting dilution method is conducted, so that screening for and monocloning of hybridomas that produce a target antibody are performed.

In addition to a method with which the above hybridomas are obtained by immunizing non-human animals with antigens, desired human antibodies having binding activity to glypican 3 can also be obtained (see Japanese Patent Publication (Kokoku) No. 1-59878 B (1989)) by sensitizing in vitro human lymphocytes with glypican 3, and causing the sensitized lymphocytes to fuse with the human-derived myeloma cells having a permanent division potential. Moreover, glypican 3 as an antigen is administered to a transgenic animal having all the repertories of a human antibody gene to obtain anti-glypican 3 antibody-producing cells, and then human antibodies for glypican 3 may be obtained from the immortalized anti-glypican 3 antibody-producing cells (see International Patent Publication Nos. WO 94/25585, WO 93/12227, WO 92/03918 and WO 94/02602).

The thus prepared hybridomas producing monoclonal antibodies can be passage-cultured in a standard culture solution, or can be stored for a long period in liquid nitrogen.

One example of a method employed to obtain monoclonal antibodies from the hybridomas involves culturing the hybridomas and obtaining monoclonal antibodies in the culture supernatant according to a standard method. Another method involves administering the hybridomas to mammals that are compatible with the hybridomas to cause them to proliferate, and obtaining monoclonal antibodies in the ascites. The former method is suitable to obtain antibodies of high purity. On the other hand, the latter method is suitable for the mass production of antibodies.

3. Recombinant Antibody

A monoclonal antibody that can be used in the present invention is a recombinant monoclonal antibody that is prepared by cloning the antibody gene from the hybridoma, incorporating the gene into an appropriate vector, introducing the vector into a host, and then causing the host to produce the recombinant monoclonal antibodies by genetic engineering techniques (e.g., see Vandamme, A. M. et al., Eur. J. Biochem. (1990) 192, 767-775, 1990). Specifically, mRNA encoding the variable (V) region of an anti-glypican 3 antibody is isolated from a hybridoma producing the anti-glypican 3 antibody. mRNA is isolated by a known method such as a guanidine ultracentrifugal method (Chirgwin, J. M. et al., Biochemistry (1979) 18, 5294-5299) or an AGPC method (Chomczynski, P et al., Anal. Biochem. (1987) 162, 156-159), thereby preparing total RNA. Target mRNA is then prepared using an mRNA Purification Kit (Pharmacia) or the like. In addition, mRNA can also be directly prepared using a QuickPrep mRNA Purification Kit (Pharmacia).

The cDNA of the antibody V region is synthesized using reverse transcriptase from the thus obtained mRNA. cDNA is synthesized using an AMV Reverse Transcriptase First-strand cDNA Synthesis Kit (SEIKAGAKU CORPORATION) or the like. In addition, to synthesize and amplify cDNA, for example, a 5'-Ampli FINDER RACE Kit (Clontech) and the 5'-RACE method using PCR (Frohman, M. A. et al., Proc. Natl. Acad. Sci. USA (1988) 85, 8998-9002, Belyaysky, A. et al., Nucleic Acids Res. (1989) 17, 2919-2932) can be employed.

A target DNA fragment is purified from the thus obtained PCR product, and then ligated to a vector DNA. Furthermore, a recombinant vector is prepared from the product, and then the vector is introduced into *Escherichia coli* or the like, consecutively, colonies are selected, thereby preparing a desired recombinant vector. The nucleotide sequence of a target DNA is then confirmed by a known method, such as a dideoxynucleotide chain termination method.

After a DNA encoding the V region of the target anti-glypican 3 antibody is obtained, this DNA is incorporated into an expression vector containing a DNA encoding the constant region (C region) of the desired antibody.

To produce the anti-glypican 3 antibodies used in the present invention, the antibody gene is incorporated into an expression vector so that the gene is expressed under the regulation of the gene expression control region including, for example, an enhancer and a promoter. Next, a host cell is transformed with the expression vector, causing the host to express the antibody.

An antibody gene can be expressed by incorporating a DNA encoding the antibody heavy chain (H-chain) or a DNA encoding the antibody light chain (L-chain) separately into expression vectors, and then simultaneously transforming a host cell with the vectors; or by incorporating DNAs encoding the H-chain and the L-chain into a single expression vector, and then transforming a host cell with the vector (see WO 94/11523).

In addition to the above host cell, a transgenic animal can also be used to produce a recombinant antibody. For example, an antibody gene is inserted in a gene encoding a protein (e.g., goat β casein) uniquely produced in milk, thereby preparing as a fused gene. A DNA fragment containing the fused gene into which the antibody gene has been inserted is injected into a goat embryo, and then such embryo is introduced into a female goat. Desired antibodies can be obtained from the milk produced by the transgenic goat or the offspring born from the goat that has accepted the embryo. Furthermore, to increase the milk volume containing the desired antibody produced by the transgenic goat, hormones can be administrated for the transgenic goat (Ebert, K. M. et al., Bio/Technology (1994) 12, 699-702).

4. Altered Antibody

In the present invention, in addition to the above antibody, artificially altered gene recombinant antibodies such as chimeric antibodies or humanized antibodies can be used for, for example, lowering heteroantigenicity against a human. These altered antibodies can be produced using a known method.

Chimeric antibodies can be obtained by ligating the DNA encoding the above antibody V-region to a DNA encoding a human antibody C-region, incorporating the product into an expression vector, and then introducing the vector into a host to cause the host to produce the antibodies. Using this known method, chimeric antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication No. EP 125023 and WO 96/02576).

Specifically, the DNA sequence is synthesized by the PCR method using as primers several oligonucleotides that have been prepared to have a portion overlapping the terminal regions of both mouse antibody CDR and the framework region (FR) of a human antibody (see the method as described in WO 98/13388).

The framework region ligated to the CDR having a good antigen binding site is selected. Amino acids in the framework region in the antibody variable region may be substituted as required, so that the CDR of a reshaped human antibody forms an appropriate antigen-binding site (Sato, K. et al., Cancer Res. (1993) 53, 851-856).

Regions of a human antibody are used for the C regions of a chimeric antibody and a humanized antibody. For example, for the H-chain, Cγ1, Cγ2, Cγ3 or Cγ4C, and for the L-chain, Cκ or Cλ can be used. In addition, to improve the stability of antibodies or the production thereof, the human antibody C-region may be modified.

A chimeric antibody consists of the variable region of an antibody derived from a mammal other than a human, and a constant region derived from a human antibody. In the meantime, a humanized antibody consists of the CDR of an antibody derived from a mammal other than a human, and the framework region and C region derived from a human antibody. Since the antigenicity of the humanized antibody is designed to be low in a human body, it is useful as an active ingredient of a therapeutic agent of the present invention.

5. Modified Antibody

The antibody used in the present invention is not limited to the whole molecule as long as it binds to glypican 3 and suppresses cell proliferation, and may be a fragment of the antibody or the modified product thereof. Both a bivalent antibody and a monovalent antibody are included. Examples of the fragment of an antibody include Fab, F(ab')2, Fv, Fab/c having one Fab and a complete Fc, and a single chain Fv (scFv) wherein the Fv of the H-chain or the L-chain is ligated with an appropriate linker. Specifically, an antibody fragment is synthesized by treating the antibody with an enzyme such as papain or pepsin, or genes encoding these antibody fragments are constructed, the genes are introduced into expression vectors, and the genes are then expressed by appropriate host cells (see e.g., Co., M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, and Bird, R. E. et al., TIBTECH (1991) 9, 132-137).

scFv is obtained by linking the H-chain V-region and the L-chain V-region of antibodies. In the scFv, the H-chain V-region and the L-chain V-region are linked via a linker, or preferably a peptide linker (Huston, J. S. et al., Proc. Natl. Acad. Sci. U.S.A. (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

A DNA encoding scFv can be obtained as follows. Amplification is performed by the PCR method using as templates the entire or DNA portions encoding desired amino acid sequences (of a DNA encoding the H-chain or the H-chain V-region of the above antibody, and a DNA encoding the L-chain or the L-chain V-region), and using a primer pair that specifies both ends. Amplification is then further performed by a combined use of a DNA encoding a peptide linker portion and a primer pair that specify to cause both ends to ligate respectively to the H-chain and L-chain.

Furthermore, once a DNA encoding scFv is prepared, expression vectors containing the DNAs, and hosts transformed with the expression vectors, can be obtained according to the standard method. In addition, by the use of the host, scFv can be obtained according to the standard method.

These antibody fragments can be produced using hosts by obtaining the genes thereof in a manner similar to the above method, and then causing the expression of the genes. The "antibody" in the present invention also encompasses these antibody fragments.

As a modified antibody, anti-glypican antibodies bound to polyethylene glycol (PEG) or one of various molecules such as a cytotoxic substance can be used. The "antibody" in the present invention also encompasses these modified antibodies. Such a modified antibody can be obtained by chemically modifying the obtained antibody. In addition, an antibody modification method has already been established in the art.

Furthermore, the antibody used in the present invention may be a bispecific antibody. The bispecific antibody may have antigen-binding sites that recognize a different epitope on a glypican 3 molecule. Alternatively, one antigen-binding site may recognize glypican 3 and the other antigen-binding site may recognize a cytotoxic substance such as a chemotherapeutant, toxin derived from cells, radioactive substance or the like. In this case, a cytotoxic substance is allowed to directly act on a cell expressing glypican 3 to specifically damage tumor cells, so that tumor cell proliferation can be suppressed. A bispecific antibody can be prepared by binding H-L pairs of two types of antibodies, and it can also be obtained by fusing hybridomas producing different monoclonal antibodies to prepare bispecific antibody-producing fused cells. Furthermore, a bispecific antibody can also be prepared by genetic engineering techniques.

6. Expression and Production of Recombinant Antibody or Modified Antibody

Antibody genes constructed as described above can be expressed and thus obtained by a known method. In the case of mammalian cells, a gene can be expressed by operably linking a useful promoter that is generally employed and the antibody gene to be expressed, and by linking a polyA signal downstream on the 3' side thereof. A promoter/enhancer is, for example, a human cytomegalovirus immediate early promoter/enhancer.

Furthermore, examples of another promoter/enhancer that can be used in the present invention for antibody expression include a virus promoter/enhancer such as a retrovirus, a polyoma virus, an adenovirus or a simian virus 40 (SV40), or a promoter/enhancer derived from a mammalian cell such as human elongation factor 1a (HEF1a).

When a SV40 promoter/enhancer is used, gene expression can be readily performed by the method of Mulligan et al (Nature (1979) 277, 108) and when a HEF1a promoter/enhancer is used, gene expression can be readily performed by the method of Mizushima et al (Nucleic Acids Res. (1990) 18, 5322).

In the case of *Escherichia coli*, a useful promoter that is generally used, a signal sequence for antibody secretion, and an antibody gene to be expressed are operably linked, so that the gene can be expressed. Examples of a promoter include a lacz promoter and an araB promoter. When the lacz promoter is used, the antibody gene can be expressed by the method of Ward et al (Nature (1098) 341, 544-546; FASEB J. (1992) 6, 2422-2427), or when the araB promoter is used, the antibody gene can be expressed by the method of Better et al (Science (1988) 240, 1041-1043).

As a signal sequence for the antibody secretion, a pelB signal sequence (Lei, S. P. et al J. Bacteriol. (1987) 169, 4379) may be used when the antibody is produced in the periplasm of *Escherichia coli*. After antibodies produced in the periplasm are isolated, the structure of the antibody is appropriately refolded and used.

A replication origin that can be used is derived from a SV40, a polyoma virus, an adenovirus, a bovine papilloma virus (BPV) or the like. Furthermore, to amplify the number of gene copies in a host cell system, an expression vector can contain an aminoglycoside transferase (APH) gene, a thymidine kinase (TK) gene, an *Escherichia coli* xanthine guanine phosphoribosyltransferase (Ecogpt) gene, a dihydrofolate reductase (dhfr) gene or the like as a selection marker.

To produce the antibodies used in the present invention, any expression systems such as a eukaryotic cell system or a prokaryotic cell system can be used. Examples of eukaryotic cells include animal cells such as cells of an established mammalian cell system or an insect cell system, and filamentous fungus cells and yeast cells. Examples of prokaryotic cells include bacterial cells such as *Escherichia coli* cells.

Preferably, antibodies used in the present invention are expressed in mammalian cells such as CHO, COS, myeloma, BHK, Vero or HeLa cells.

Next, a transformed host cell is cultured in vitro or in vivo, so as to cause the host cell to produce a target antibody. Host cells are cultured according to a known method. For example, as a culture solution, DMEM, MEM, RPMI1640, IMDM or the like can be used. A serum fluid such as fetal calf serum (FCS) can be used in combination.

7. Separation and Purification of Antibody

The antibodies expressed and produced as described above can be isolated from the cells or host animals, and purified to a uniform level. Isolation and purification of the antibodies to be used in the present invention can be performed using affinity columns. An example of a column using a protein A column is a Hyper D, POROS, Sepharose F.F. (Pharmacia). Other standard isolation and purification methods that are employed for proteins may be used, and there is no limitation regarding their use. For example, a chromatography column other than the above affinity column, a filter, ultrafiltration, a method of salting out, dialyses and the like may be appropriately selected and combined for use, so that antibodies can be isolated and purified (Antibodies A Laboratory Manual. Ed Harlow, David Lane, Cold Spring Harbor Laboratory, 1988).

8. Confirmation of Antibody Activity

Known means can be employed to assay the antigen-binding activity of the antibody used in the present invention (Antibodies A Laboratory Manual. Ed Harlow, David Lane, Cold Spring Harbor Laboratory, 1988) and activity to inhibit ligand receptor binding (Harada, A. et al., International Immunology (1993) 5, 681-690).

As a method to measure the antigen-binding activity of the anti-glypican 3 antibody used in the present invention, ELISA (enzyme-linked immunosorbent assay), EIA (enzyme immunoassay), RIA (radioimmunoassay) or the fluorescent antibody technique can be employed. For example, when enzyme immunoassay is employed, a sample containing anti-glypican 3 antibodies, such as the culture supernatant of anti-glypican 3 antibody-producing cells or purified antibodies are added to a plate coated with glypican 3. A secondary antibody labeled with an enzyme such as alkaline phosphatase is added. The plate is then incubated and then washed, an enzyme substrate such as p-nitrophenyl phosphoric acid is added, and then absorbance is measured, so that antigen-binding activity can be evaluated.

To confirm the activity of the antibody used in the present invention, the neutralization activity of an anti-glypican 3 antibody is measured.

9. Cytotoxic Activity

The antibodies used in the present invention have ADCC activity or CDC activity as cytotoxic activity.

ADCC activity can be measured by mixing effector cells, target cells and anti-glypican 3 antibodies, and then examining the degree of ADCC. As effector cells, for example, mouse splenocytes, human peripheral blood or monocytes isolated from the bone marrow can be used. As target cells, for example, human established cell lines such as HuH-7 human hepatic cancer cell line can be used. Target cells are previously labeled with $^{51}$Cr, anti-glypican 3 antibodies are added to the cells, and then incubation is performed. Next, effector cells are added at an appropriate ratio of the cells to the target cells, and then incubation is performed. After incubation, the supernatant is collected and radioactivity in the supernatant is counted, so that ADCC activity can be measured.

CDC activity can be measured by mixing the above labeled target cells and anti-glypican 3 antibodies, adding complements, performing incubation, culturing, and then counting radioactivity in the supernatant.

Antibodies need an Fc portion to exert cytotoxic activity. When the cell growth inhibitor of the present invention utilizes the cytotoxic activity of an antibody, the anti-glypican 3 antibody used in the present invention is required to contain the Fc portion.

10. Inhibition of Vascularization

The anti-glypican 3 antibody of the present invention can be used to inhibit vascularization.

11. Administration Method and Pharmaceutical Preparation

The cell growth inhibitor of the present invention is used to treat or improve conditions arising from disease based on abnormal cell proliferation, and particularly, cancer.

Preferred examples of the target carcinoma cells of the cell growth inhibitor of the present invention include, but are not specifically limited to, hepatic cancer cells, lung cancer cells, colon cancer cells, mammary cancer cells, prostate cancer cells, leukemia cells, lymphoma cells and pancreatic cancer cells. Hepatic cancer cells are particularly preferred.

Effective dose is selected from the range of 0.001 mg to 1000 mg per kg in body weight per administration. Alternatively, a dose in the range of 0.01 to 100000 mg/body per patient can be selected. However, the dose of the therapeutic agent containing anti-glypican 3 antibodies of the present invention is not limited to these doses.

Furthermore, as the dosage time of the therapeutic agent of the present invention, the agent can be administered either before or after the onset of the clinical symptoms of a disease.

The therapeutic agent containing anti-glypican 3 antibodies as an active ingredient of the present invention can be formulated according to standard methods (Remington's Pharmaceutical Science, latest edition, Mark Publishing Company, Easton, U.S.A.), and may contain a pharmaceutically acceptable carrier and an additive together.

Examples of such carriers and pharmaceutical additives include water, a pharmaceutically acceptable organic solvent, collagen, polyvinyl alcohol, polyvinylpyrrolidone, carboxyvinyl polymer, sodium carboxymethylcellulose, sodium polyacrylate, sodium alginate, water-soluble dextran, sodium carboxymethylstarch, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactant that is acceptable as a pharmaceutical additive.

One or an appropriate combination of the above additives is practically selected according to the dosage form of the therapeutic agent of the present invention, but is not limited thereto. For example, the agent that can be used as a pharmaceutical preparation for injection can be prepared by dissolving purified anti-glypican 3 antibodies in a solvent such as a physiological saline, a buffer or a glucose solution, and then adding an adsorption inhibitor such as Tween80, Tween20, gelatine or human serum albumin to the solution. Alternatively, the freeze-dried agent may be used to prepare a dosage form that is dissolved for reconstitution before use. As an excipient for freeze-drying, for example, sugar alcohol or saccharides such as mannitol or glucose can be used.

BEST MODE FOR CARRYING OUT THE INVENTION

Figure 1:
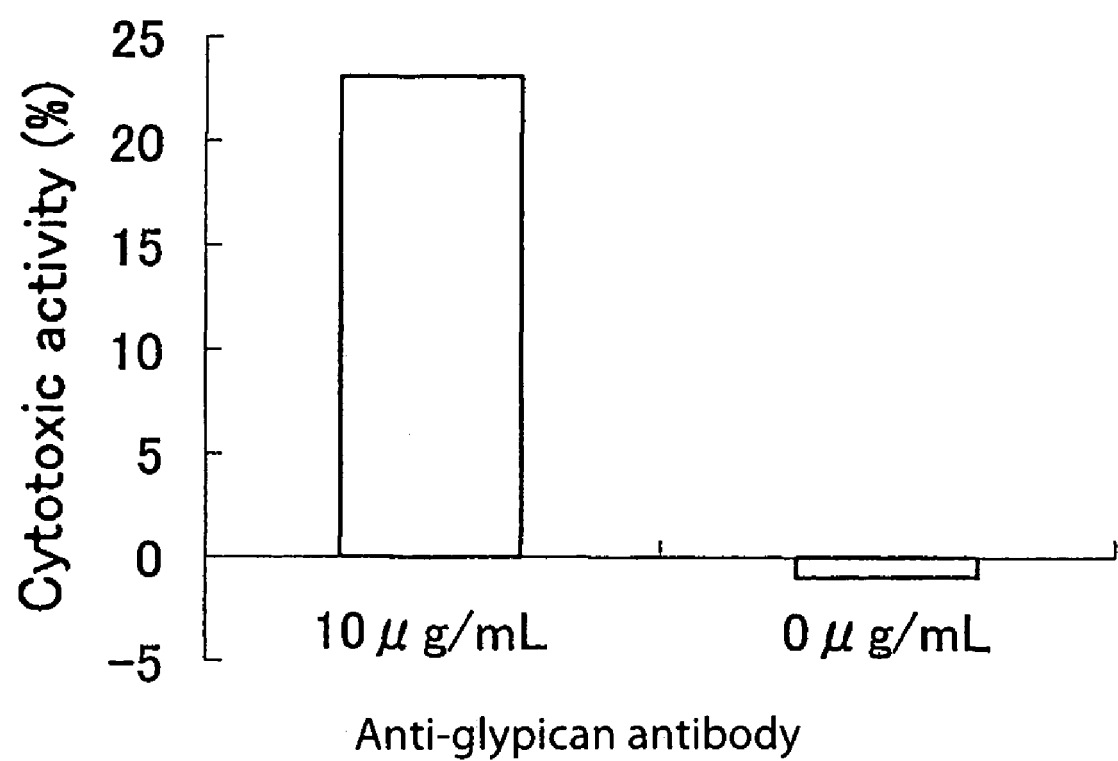
FIG. 1 shows ADCC activity on HuH-7 cells of anti-glypican 3 antibodies (K6534).

The present invention will be further described in reference to the following examples. However, the technical scope of the present invention is not limited by these examples or the like.

Example 1

Preparation of Monoclonal Antibody Against Glypican-3 Synthetic Peptide

A peptide having an amino acid sequence (the 355th to the 371st amino acids) (Arg Gln Tyr Arg Ser Ala Tyr Pro Glu Asp Leu Phe Ile Asp Lys Lys) of human glypican-3 protein (SEQ. ID NO. 1) was synthesized. The synthetic peptide was bound to keyhole limpet hemocyanin (KLH) using a maleinimide benzoyloxy succinimide (MBS) type crosslinking agent, thereby preparing an immunogen. Mice (BALB/c, female, 6-week-old) were immunized 3 times with the immunogen at 100 µg/mouse. The antibody titers in serum were assayed. A method employed as an antibody titer assay method involves causing the diluted sera to react with the peptides (0.5 µg) immobilized on a plate, performing reaction with HRP-labeled anti-mouse antibodies, adding a substrate, and then measuring absorbance at 450 nm of the thus developed color (a peptide solid-phase ELISA method). After antibody titers were confirmed, splenocytes were collected, and then fused (Köhler, G, Milstein, C: Nature, 256: 495 (1975)) with myeloma cells (P3/X63-Ag8), thereby preparing hybridomas. Monoclonal antibodies produced by five types of hybridomas were then purified. The binding activity to the peptide was measured using the peptide solid-phase ELISA method, and then IgG1 antibodies (hereinafter, K6534) and IgG3 antibodies (hereinafter, K6511) having high binding activity were selected.

Example 2

Inhibition of Cell Proliferation Using Anti-Glypican 3 Antibody

The ADCC (antibody-dependent cell-mediated cytotoxicity) activity and the CDC (complement-dependent cytotoxicity) activity were measured according to the method of Current Protocols in Immunology, Chapter 7. Immunologic studies in humans, Editor, John E, Cologan et al., John Wiley & Sons, Inc., 1993.

1. Preparation of Effector Cell

The spleen was extracted from a CBA/N mouse (8-week-old, male), and then splenocytes were isolated in RPMI1640 media (GIBCO). The cells were washed in the same media containing 10% fetal bovine serum (FBS, HyClone), and then the cell concentration was prepared at $5 \times 10^6$/mL, thereby preparing effector cells.

2. Preparation of Complement Solution

Baby Rabbit Complement (CEDARLANE) was diluted 10 times in 10% FBS-containing DMEM media (GIBCO), thereby preparing a complement solution.

3. Preparation of Target Cell

An HuH-7 human hepatic cancer cell line (Japanese Collection of Research Bioresources (JCRB) No. JCRB0403, Human Science Research Support Bank (Human Science Kenkyu Shien Bank)) was cultured with 0.2 mCi of $^{51}$Cr-sodium chromate (Amersham Pharmacia Biotech) in 10% FBS-containing DMEM media at 37° C. for 1 hour, thereby performing radioactive labeling. After radioactive labeling, the cells were washed 3 times in 10% FBS-containing RPM11640 media, the cell concentration was prepared at $2 \times 10^5$/mL, thereby preparing target cells.

4. Measurement of ADCC Activity

50 µL each of the target cells and anti-glypican 3 antibodies (K6534) were added to a 96-well U-bottomed plate (Beckton Dickinson), and then allowed to react on ice for 15 minutes. 100 µL of effector cells was then added, and then cultured within a carbon dioxide gas incubator for 4 hours. The final concentration of the antibodies was prepared at 0 or 10 µg/mL. After culturing, 100 µL of the supernatant was collected, and then radioactivity was measured using a gamma counter (COBRA II AUTO-GAMMA, MODEL D5005, Packard Instrument Company). Cytotoxic activity (%) was found by using the formula (A−C)/(B−C)×100. Therein, "A" represents radioactivity (cpm) in each sample, "B" represents radioactivity (cpm) in a sample supplemented with 1% NP-40 (nacalai tesque), and "C" represents radioactivity (cpm) in a sample containing only target cells. The experiment was performed in duplicate, and average values were calculated.

5. Measurement of CDC Activity

50 µL each of the target cells and anti-glypican 3 antibodies (K6511) were added to a 96-well flat-bottomed plate (Becton Dickinson), and then allowed to react on ice for 15 minutes. 100 µL of a complement solution was then added, followed by 4 hours of culturing in a carbon dioxide gas incubator. The final concentration of the antibody was 0 or 3 µg/mL. After culturing, 100 µL of the supernatant was collected, and then radioactivity was measured using a gamma counter. Cytotoxic activity (%) was found in the same manner as that used in "4. Measurement of ADCC activity." The experiment was performed in duplicate, and average values were calculated.

Figure 2:
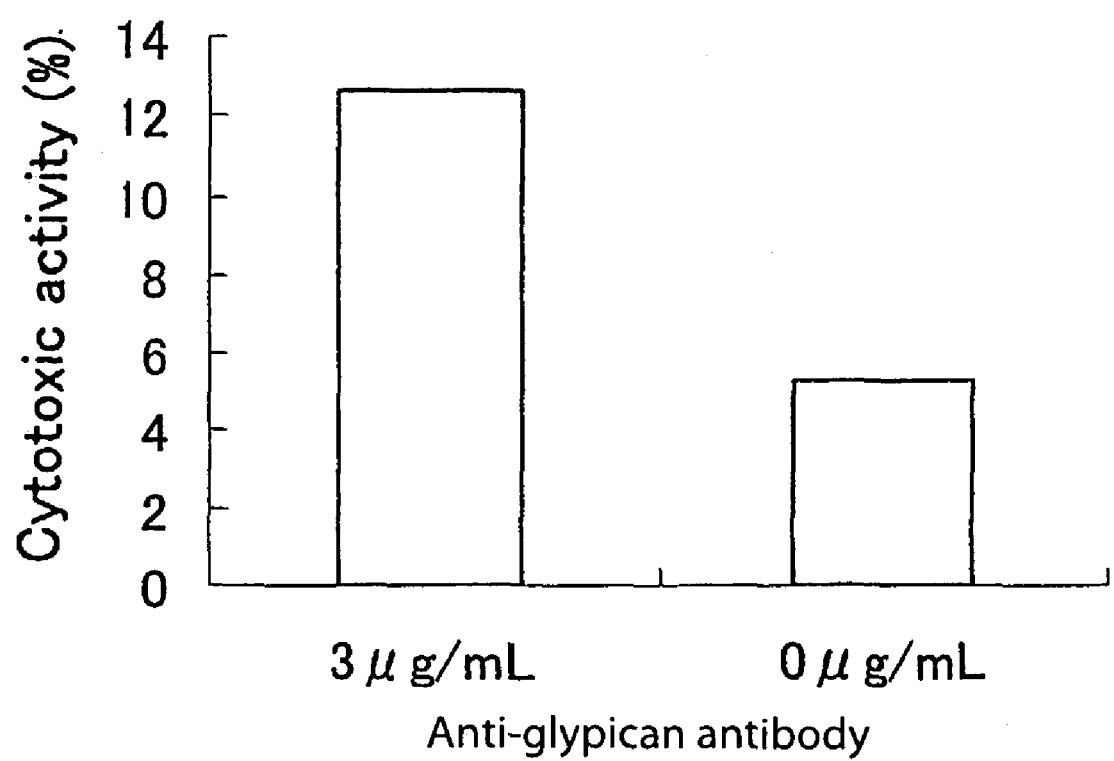
FIG. 2 shows CDC activity on HuH-7 cells of anti-glypican 3 antibodies (K6511).

FIG. 1 shows ADCC activity and FIG. 2 shows CDC activity. These results revealed that anti-glypican 3 antibodies exert ADCC activity and CDC activity on an HuH-7 human hepatic cancer cell line and thus inhibit cell proliferation.

Example 3

Measurement of the Expression Level of Glypican on HuH-7 Cells

Approximately 5×10$^5$ HuH-7 cells were suspended in 100 μL of FACS/PBS (prepared by dissolving 1 g of bovine serum albumin (SIGMA) in 1 L of CellWASH (Beckton Dickinson)). Then, anti-glypican 3 antibodies (K6511) or mouse IgG2a (Biogenesis) as a control antibody were added at 25 μg/mL, and then the solution was allowed to stand on ice for 30 minutes. After washing with FACS/PBS, the product was suspended in 100 μL of FACS/PBS. 4 μL of Goat Anti-Mouse Ig FITC (Becton Dickinson) was added, and then the solution was allowed to stand on ice for 30 minutes.

After washing twice with FACS/PBS, the product was suspended in 1 mL of FACS/PBS. Fluorescence intensity of the cells was measured using a flow cytometer (EPICS XL, BECKMAN COULTER).

Figure 3:
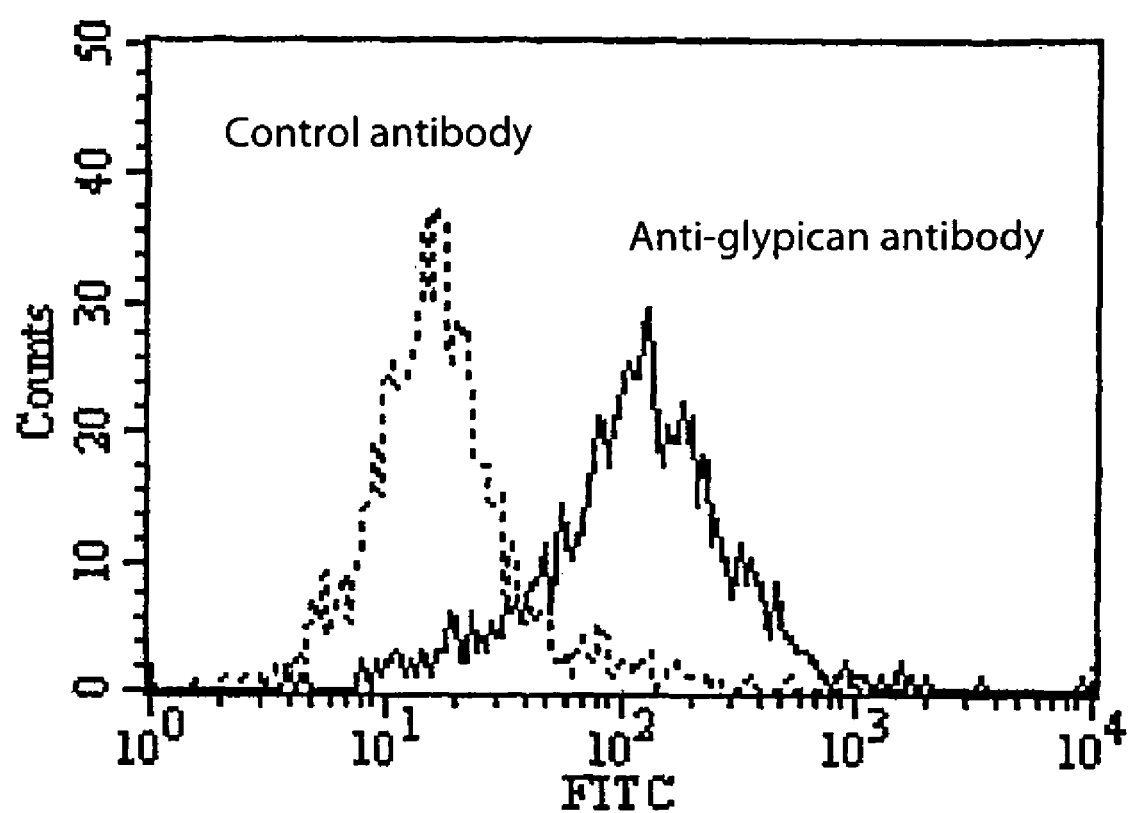
FIG. 3 shows the expression of glypican on HuH-7 cells.
Figure 4A:
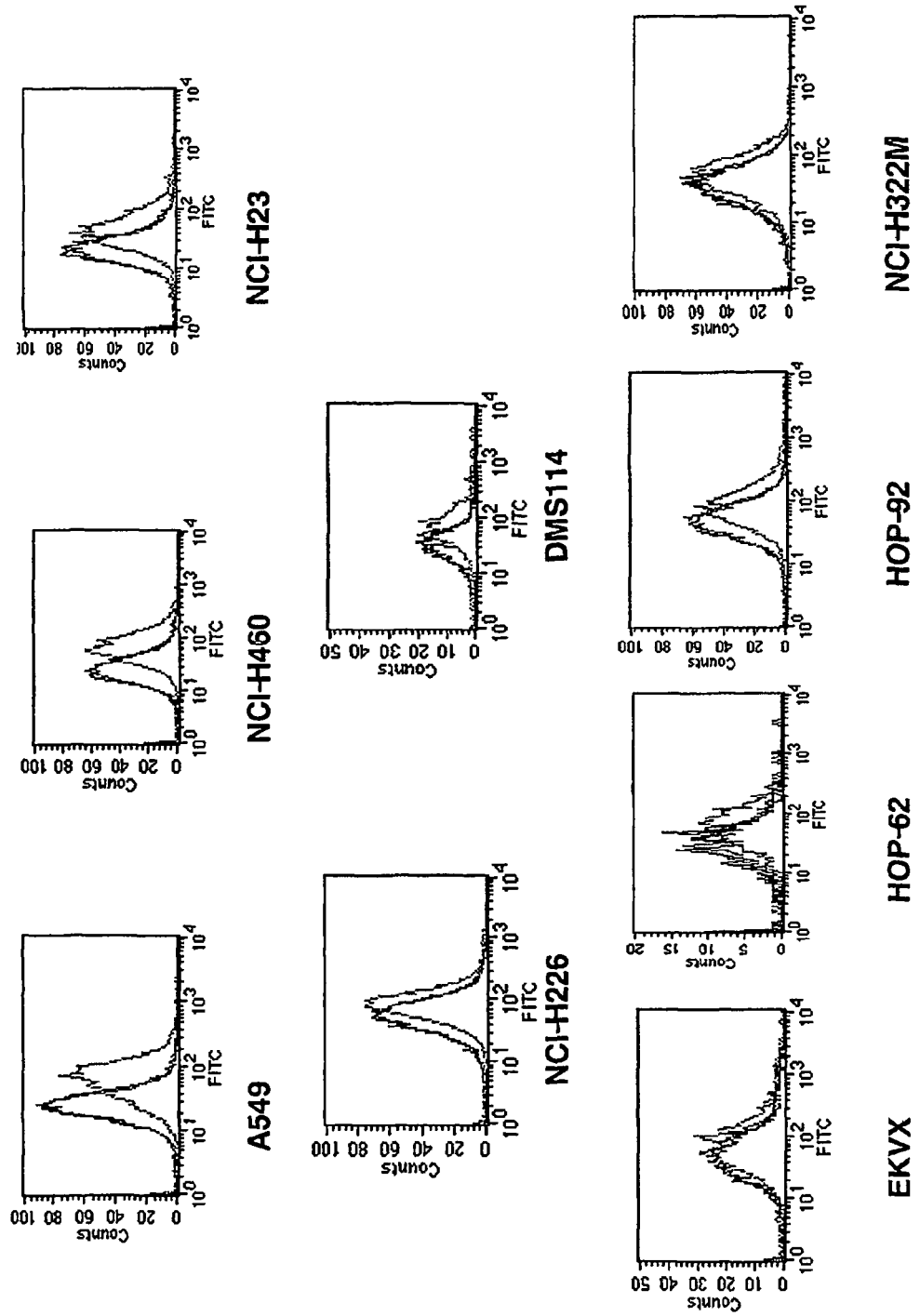
FIG. 4A shows the results of FACS analysis of GPC3 expression by human lung cancer cell lines. They are the results of analyses with anti-glypican 3 antibodies (K6534).
Figure 4B:
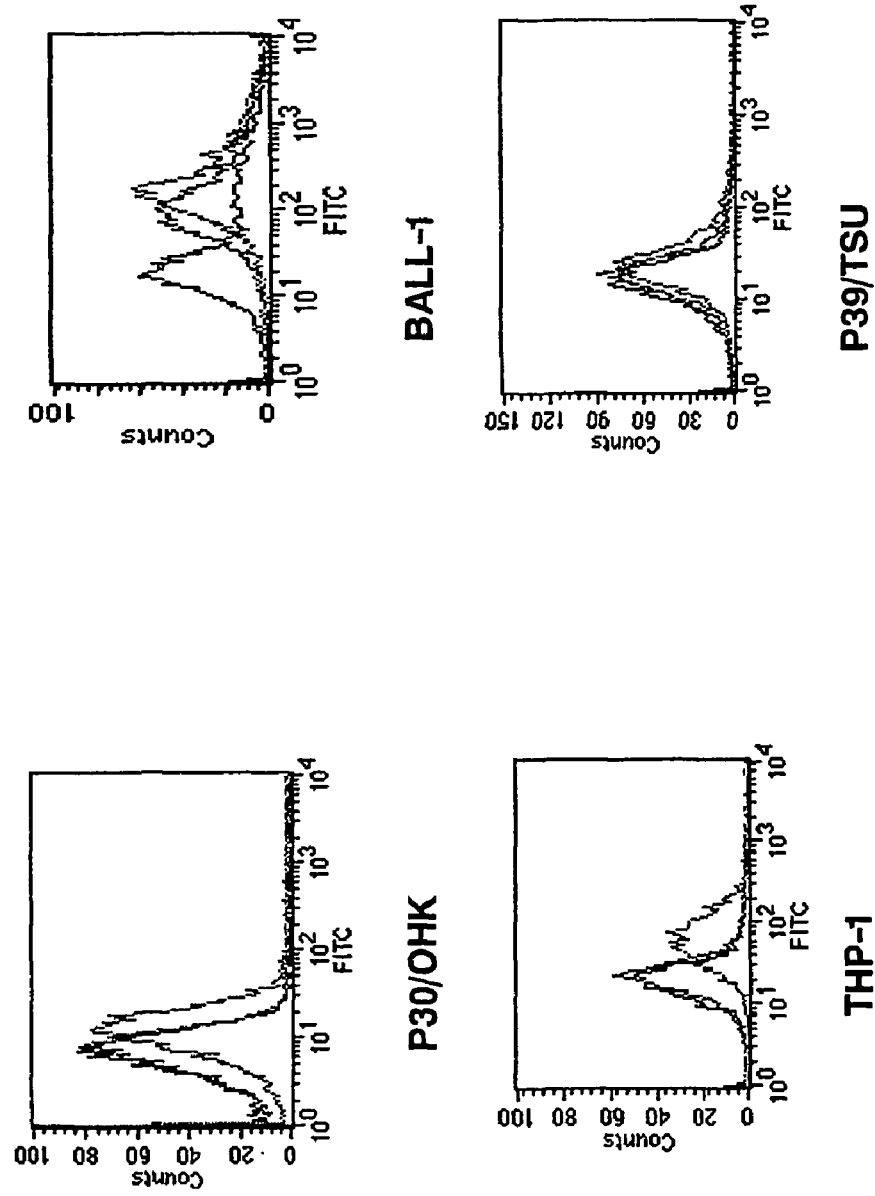
FIG. 4B shows the results of FACS analysis of GPC3 expression by human leukemia cell lines. They are the results of analyses with anti-glypican 3 antibodies (K6534).
Figure 4C:
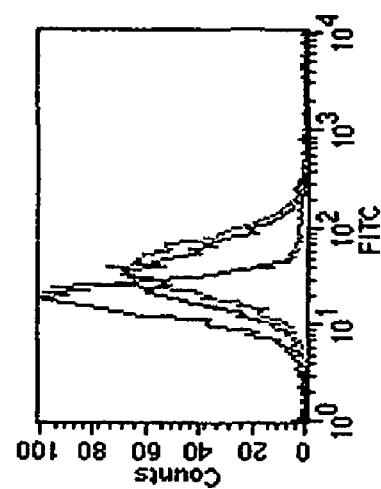
FIG. 4C shows the results of FACS analysis of GPC3 expression by human lymphoma cell lines. They are the results of analyses with anti-glypican 3 antibodies (K6534).
Figure 4C:
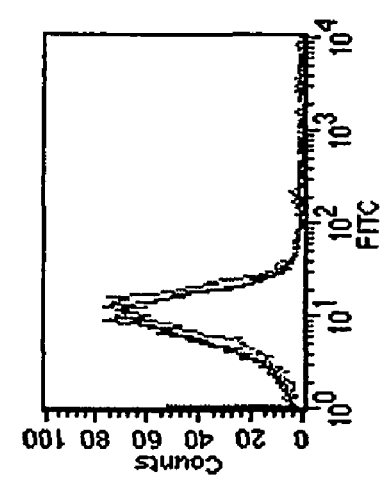
Figure 4C:
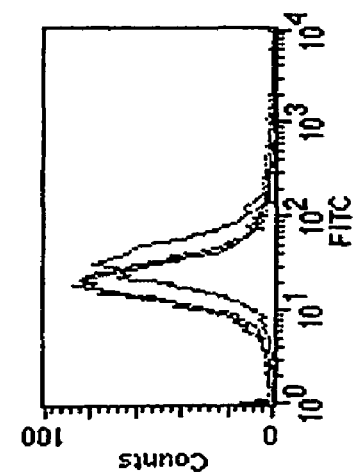
Figure 4D:
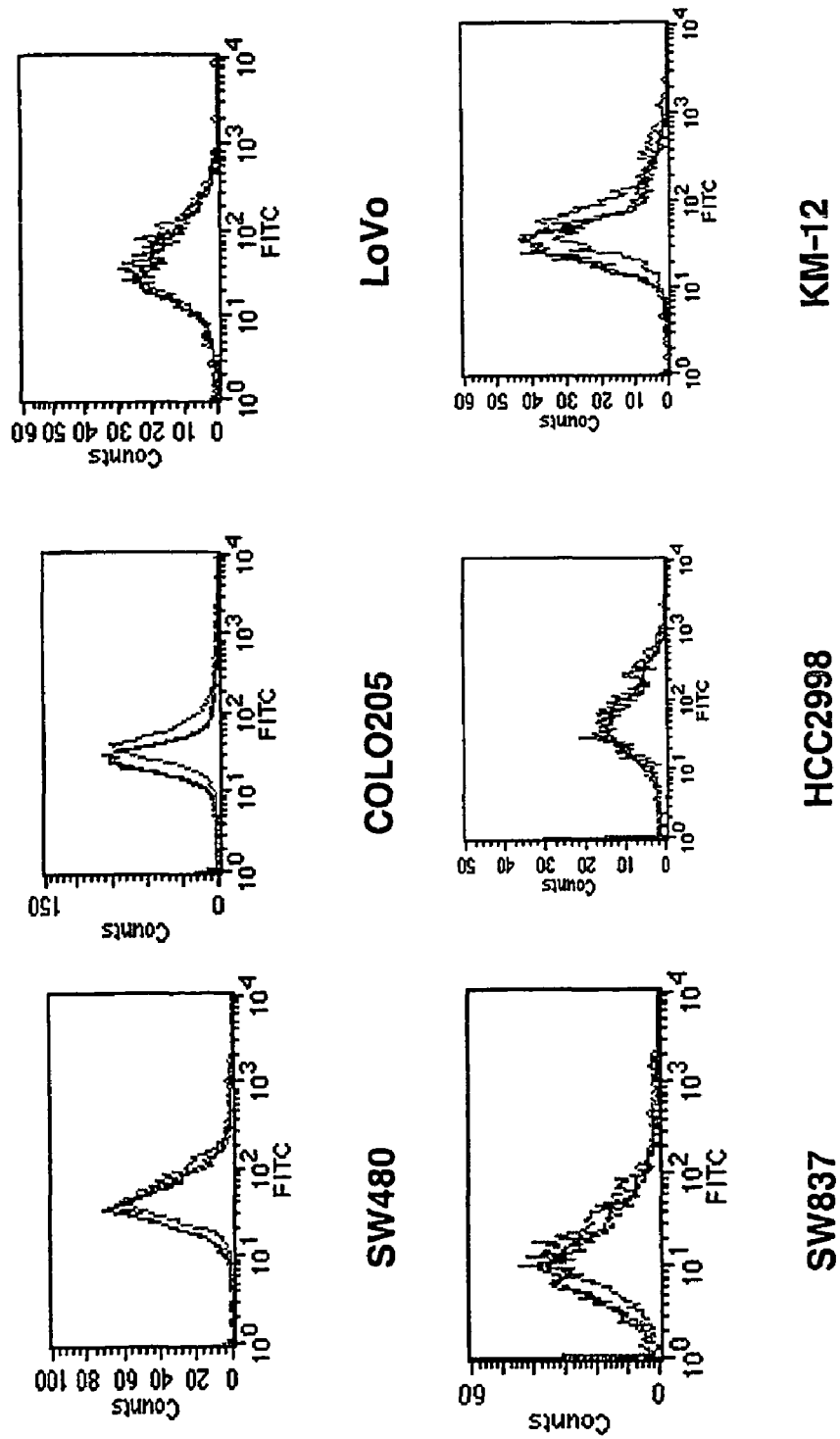
FIG. 4D shows the results of FACS analysis of GPC3 expression by human colon cancer cell lines. They are the results of analyses with anti-glypican 3 antibodies (K6534).
Figure 4E:
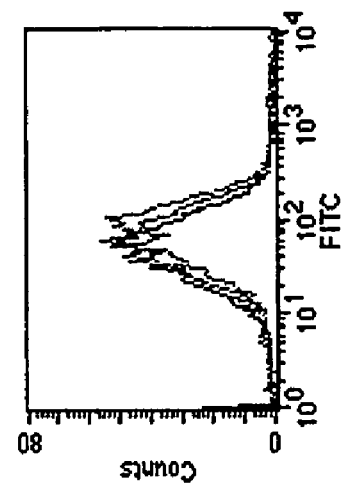
FIG. 4E shows the results of FACS analysis of GPC3 expression by human mammary cancer cell lines. They are the results of analyses with anti-glypican 3 antibodies (K6534).
Figure 4E:
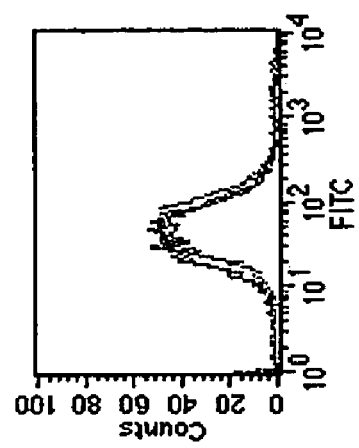
Figure 4E:
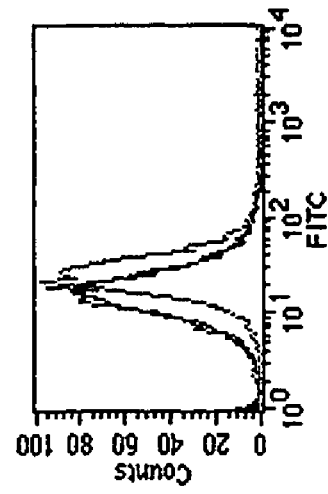
Figure 4F:
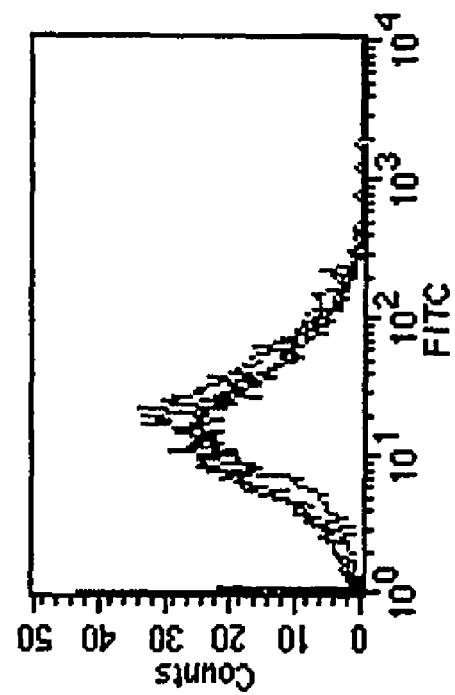
FIG. 4F shows the results of FACS analysis of GPC3 expression by human prostate cancer cell lines. They are the results of analyses with anti-glypican 3 antibodies (K 6534).
Figure 4F:
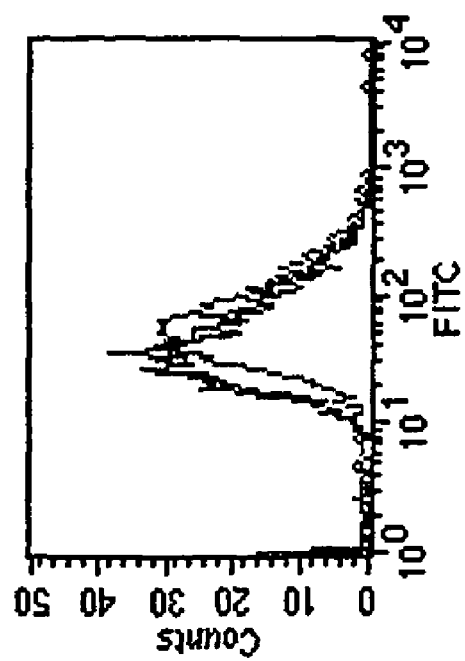
Figure 4G:
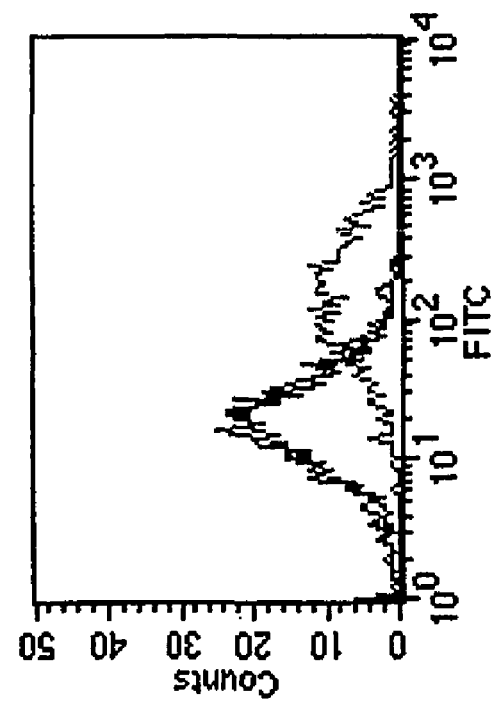
FIG. 4G shows the results of FACS analysis of GPC3 expression by the human pancreatic cancer cell line and the human hepatic cancer cell line. They are the results of analyses with anti-glypican 3 antibodies (K6534).
Figure 4G:
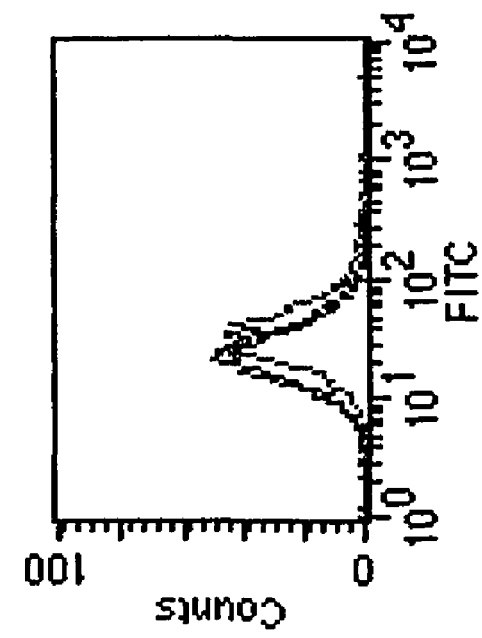

FIG. 3 shows the result of flow cytometry. Glypican 3 was expressed on HuH-7 cells, suggesting that anti-glypican 3 antibodies bind to glypican 3 expressed on the cell so as to inhibit cell proliferation (FIG. 3).

Example 4

GPC3 Expression Analysis on Carcinoma Cell Panel Using FCM

Expression of glypican 3 (GPC3) by human cancer cell lines (lung, colon, rectum, mammary, prostate, leukemia, lymphoma, myeloma, pancreas and liver) was analyzed using FCM.

The cells were cultured for 2 days and then subjected to assay. The adhered cells were collected using Trypsin-EDTA (Cat. No. 25300-054, Lot 14210, GIBCO) that had been diluted 10 times with cell dissociation buffer (Cat. No. 13150-016, Lot 1098554, GIBCO). The collected cells were allowed to react on ice with anti-glypican 3 antibodies (K6534, 600 μg/ml) or mIgG2a antibodies as a negative control (Biogenesis, M-IgG2a-i, Lot EA990719A, 1 mg/ml) (final antibody concentration of 10 μg/ml). After being washed, the cells were allowed to react with FITC-labeled anti-mouse Ig antibody (Cat. No. 349031, BD PharMingen) on ice (2 μl/test). After the cells were washed, fluorescence intensity was measured using a flow cytometer (EPICS XL, BECKMAN COULTER). As a result, the expression of GPC3 was confirmed in the lung cancer cell lines (A549, NCI-H460, NCI-H23, NCI-H226, DMS114, EKVX, HOP-62 and NCI-H322 M; the leukemia cell lines P30/OHK, BALL-1, THP-1 and P39/TSU), the lymphoma cell lines (MLMA, Ramos and U937)-; the colon cancer cell lines (SW480, COLO205, LoVo and SW837), the mammary cancer cell lines (MDA-MB-231, SK-BR-3, and MDA-MB-468), the prostate cancer cell lines (LNCaP and 22Rv1), the pancreatic cancer cell line (MIAPaCa-2), and the hepatic (liver) cancer cell line (HepG2). Based on these results, it is concluded that the cell growth inhibitor of the present invention is useful in treating lung cancer, colon cancer, mammary cancer, prostate cancer, leukemia, lymphoma, pancreatic cancer and the like.

INDUSTRIAL APPLICABILITY

According to the present invention, a cell growth inhibitor containing an anti-glypican 3 antibody as an active ingredient is provided. Moreover, according to the present invention, a carcinoma cell growth inhibitor containing an anti-glypican 3 antibody as an active ingredient is provided. The anti-glypican 3 antibody binds to glypican 3 that is expressed on HuH-7 cells of a human hepatic cancer cell line, so as to inhibit cell proliferation. Thus, the agent containing the anti-glypican 3 antibody is useful as a cell growth inhibitor, and in particular a carcinoma cell inhibitor.

All publications, patents and patent applications cited herein are incorporated herein by reference in their entirety. It is therefore readily to be understood by a person skilled in the art that numerous modifications and variations of the present invention are possible within the scope of the invention without departing from the technical idea and the scope of the invention as described in the appended claims. The present invention is intended to encompass such modifications and variations.

The invention claimed is:

1. A method of treating lung cancer comprising administering to a patient in need thereof a pharmaceutical composition containing an anti-glypican 3 antibody as an active ingredient wherein the anti-glypican 3 antibody has cytotoxic activity.

2. The method of claim 1, wherein the cytotoxic activity is antibody-dependent cell-mediated cytotoxicity (ADCC) activity.

3. The method of claim 1, wherein the cytotoxic activity is complement-dependent cytotoxicity (CDC) activity.

4. The method of claim 1, wherein the anti-glypican 3 antibody is a humanized antibody.

5. The method of claim 1, wherein the anti-glypican 3 antibody is a chimeric antibody.

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: homo sapiens

<400> SEQUENCE: 1

Arg Gln Tyr Arg Ser Ala Tyr Pro Glu Asp Leu Phe Ile Asp Lys Lys
1               5                   10                  15
```